(12) United States Patent
Lee et al.

(10) Patent No.: US 9,199,950 B2
(45) Date of Patent: Dec. 1, 2015

(54) METHOD FOR PRODUCING GLYCIDOL BY SUCCESSIVE CATALYTIC REACTIONS

(71) Applicant: KOREA INSTITUTE OF SCIENCE AND TECHNOLOGY, Seoul (KR)

(72) Inventors: Hyun Joo Lee, Gyeonggi-do (KR); Byoung Sung Ahn, Seoul (KR); Sang Deuk Lee, Seoul (KR); Jungho Jae, Seoul (KR); Ji Sik Choi, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 14/313,153

(22) Filed: Jun. 24, 2014

(65) Prior Publication Data

US 2015/0239858 A1 Aug. 27, 2015

(30) Foreign Application Priority Data

Feb. 27, 2014 (KR) .......................... 10-2014-0223450

(51) Int. Cl.
*C07D 301/02* (2006.01)
*C07D 317/36* (2006.01)

(52) U.S. Cl.
CPC ............ *C07D 301/02* (2013.01); *C07D 317/36* (2013.01)

(58) Field of Classification Search
CPC ............................ C07D 301/02; C07D 317/36
USPC ......................................................... 549/518
See application file for complete search history.

(56) References Cited

U.S. PATENT DOCUMENTS

| 2,856,413 | A | * | 10/1958 | Malkemus et al. | ........... | 549/518 |
| 2,915,529 | A | | 12/1959 | Bell, Jr., et al. | | |
| 6,316,641 | B1 | * | 11/2001 | Yoo et al. | ...................... | 549/519 |

FOREIGN PATENT DOCUMENTS

| JP | 2009-067689 A | 4/2009 |
| JP | 2009-137938 A | 6/2009 |

OTHER PUBLICATIONS

Gade et al, Synthesis of Glycidol from glycerol and dimethyl carbonate using ionic liquid as a catalyst, Catalysis Communications, 2012, vol. 27, p. 184-188.*
Ji Sik Choi et al; "Ionic-liquid-catalyzed decarboxylation of glycerol carbonate to glycidol", Journal of Catalysis, vol. 297, pp. 248-255; Available online Nov. 17, 2012.

(Continued)

*Primary Examiner* — T. Victor Oh
(74) *Attorney, Agent, or Firm* — Ladas & Parry LLP

(57) ABSTRACT

Disclosed is a method for producing glycidol by successive catalytic reactions. The method includes a series of reactions for the preparation of glycerol carbonate from glycerol and the decarboxylation of the glycerol carbonate. Specifically, the method includes i) reacting glycerol with a dialkyl carbonate to prepare glycerol carbonate, and ii) subjecting the glycerol carbonate to decarboxylation wherein a base is added as a catalyst in step i) and is allowed to react with an acid to form a metal salt after step i), and the salt is used as a catalyst in step ii). According to the method, inexpensive and easy-to-purchase acid and base catalysts can be used to produce glycidol from glycerol, a by-product of biodiesel production, as a starting material in high yield with high selectivity in a convenient, simple, and environmentally friendly way. In addition, the method eliminates the need to separate the base catalyst.

20 Claims, 2 Drawing Sheets

(56) References Cited

OTHER PUBLICATIONS

José R. Ochoa-Gómez et al: "Synthesis of glycerol carbonate from glycerol and dimethyl carbonate by transesterification: Catalyst screening and reaction optimization", Applied Catalysis A General; vol. 366, pp. 315-324; Available online Jul. 23, 2009.

Rongxian Bai, et al; "One-pot synthesis of glycidol from glycerol and dimethy carbonate over a highly efficient and easily available solid $NaAlO_2$", Green Chemistry, vol. 15, pp. 2929-2934; First published online Aug. 2, 2013.

* cited by examiner

Glycerol carbonate → Glycidol + CO$_2$

Glycerol + Dialkyll carbonate → Glycerol carbonate + 2 ROH (Methanol)

Glycerol + Urea → Glycerol carbonate + 2 NH$_3$

U10: Brine circulator  
D12: Product receiver  
TR: Temperature recorder  
PG: Pressure gauge D11: Reactor  
D13: Cold trap  
TIC: Temperature indicating controller  
FG: Flow meter E11: Condenser  
P11: Vacuum pump

METHOD FOR PRODUCING GLYCIDOL BY SUCCESSIVE CATALYTIC REACTIONS

CROSS-REFERENCE TO RELATED APPLICATIONS

This application claims priority under 35 U.S.C. §119 to Korean Patent Application No. 10-2014-0023450 filed on Feb. 27, 2014 in the Korean Intellectual Property Office, the disclosure of which is incorporated herein by reference in its entirety.

BACKGROUND OF THE INVENTION

1. Field of the Invention

The present invention relates to a method for producing glycidol through a series of reactions for the preparation of glycerol carbonate from glycerol and the decarboxylation of the glycerol carbonate.

2. Description of the Related Art

Recently, there has been a rapidly increasing demand for and interest in biodiesel as a new renewable energy source that is synthesized from vegetable oils or animal fats. Biodiesel is produced by reacting fatty acids with alcohols. Biodiesel production generates about 10% (w/w) glycerol as a by-product. An approach for high value-added products from cheap glycerol that is currently in oversupply is thermal decomposition of glycerol carbonate as glycerol derivative to synthesize glycidol. Glycidol is used in various applications, for example, cleansing agents in the petrochemical industry, materials for drug delivery, and raw materials for polymers. Glycidol is produced on an industrial scale by two methods. One method is to oxidize allyl alcohol with hydrogen peroxide in the presence of a catalyst. The other method is to treat chloropropanediol with a base. However, these methods are advantageous in terms of production yield but involve complicated purification steps to produce pure glycidol. Another disadvantage of the methods is decomposition of tungsten oxide catalysts during the catalytic reactions, incurring an increase in production cost and leading to the generation of excess wastewater and salts.

FIG. 1 shows a new method for the synthesis of glycidol by thermal decomposition of glycerol carbonate derived from glycerol. Thermal decomposition of glycerol carbonate is performed using a metal salt catalyst and produces carbon dioxide as well as glycidol. According to this method, glycerol carbonate as a glycerol derivative is subjected to decarboxylation to produce glycidol. The use of the biomass-based raw material makes the method worthy of consideration from an economic and environmental viewpoint.

Other methods for the production of glycidol as a high value-added compound from glycerol carbonate as a raw material are shown in FIGS. 2 and 3. Glycerol carbonate is an intermediate prepared by reacting glycerol with a dialkyl carbonate (FIG. 2) or urea (FIG. 3). For example, Japanese Patent Publication Nos. 2009-137938 and 2009-067689 disclose methods for producing glycidol by reacting glycerol with urea in the presence of $ZnSO_4$ as a catalyst to prepare glycerol carbonate as an intermediate, purifying the glycerol carbonate, and using the purified glycerol carbonate as a raw material for glycidol production. The preparation of glycerol carbonate from urea is advantageous in that the urea price is relatively low but has the disadvantage that it is necessary to reduce the internal pressure of a reactor using a vacuum pump in order to remove ammonia as a by-product, a long reaction time of at least 10 hours is consumed, and thin-film distillation is required to separate the catalyst after the reaction.

Another method for preparing glycerol carbonate as an intermediate for glycidol production is known in which DMC reacts with glycerol in the presence of a basic catalyst. It is known that this reaction enables the synthesis of glycerol carbonate in a yield of 80 to 90% in the presence of a homogeneous base, typically CaO or NaOH. However, there exist problems associated with the separation of glycerol carbonate from the catalyst. In view of these problems, studies on heterogeneous catalysts have been consistently conducted (Applied Catalysis A: General 366, (2009), 315-324). To the best of our knowledge, no report has appeared on methods for the production of glycidol by decarboxylation of glycerol carbonate obtained as a result of the reaction of DMC with glycerol.

The reaction for the production of glycidol through decarboxylation of glycerol carbonate takes place in high yield in the presence of an anion that forms a hydrogen bond of moderate strength with glycerol carbonate. However, in the case where catalysts used in the preparation of glycerol carbonate remain in the reactor for glycidol production, reactions occur between the catalysts, which may seriously affect the decarboxylation yield of the glycerol carbonate. In consideration of this problem, Japanese Patent Publication Nos. 2009-137938 and 2009-067689 describe the use of thin-film distillation as a process for purifying glycerol carbonate to overcome the drawbacks of high boiling point and thermal instability. However, the additional process leads to increases in energy consumption and equipment cost.

PRIOR ART DOCUMENTS

Patent Documents

Patent Document 1: Japanese Patent Publication No. 2009-137938
Patent Document 2: Japanese Patent Publication No. 2009-067689

Non-Patent Documents

Non-Patent Document 1: Applied Catalysis A: General 366, (2009), 315-324
Non-Patent Document 2: Journal of Catalysis, 297, (2013), 218-225

SUMMARY OF THE INVENTION

The present invention is intended to provide a method for producing glycidol, which is used in various applications across all industries, by successive catalytic reactions for synthesizing glycerol carbonate as an intermediate from glycidol and a dialkyl carbonate and direct decarboxylation of the glycerol carbonate without purification in which inexpensive and easy-to-purchase acid and base catalysts are used to achieve high production yield of glycidol and high selectivity to glycidol and the procedure can be performed in a convenient, simple, and environmentally friendly way, thus creating huge economic and environmental ripple effects.

According to an aspect of the present invention, there is provided a method for producing glycidol by successive catalytic reactions, including i) reacting glycerol with a dialkyl carbonate to prepare glycerol carbonate, and ii) subjecting the glycerol carbonate to decarboxylation wherein a base is added as a catalyst in step i) and is allowed to react with an acid to form a metal salt after step i), and the salt is used as a catalyst in step ii).

According to one embodiment of the present invention, the base may be selected from the group consisting of NaOH, KOH, LiOH, $R_3N$ (R is a $C_2$-$C_6$ alkyl group), and mixtures thereof.

According to a further embodiment of the present invention, in step i), the base catalyst may be added in an amount of 0.005 moles to 0.05 moles per mole of the glycerol.

According to another embodiment of the present invention, step i) may be performed at a temperature of 20° C. to 90° C.

According to another embodiment of the present invention, step i) may be performed for 3 minutes to 120 minutes.

According to another embodiment of the present invention, in step i), the dialkyl carbonate may react with the glycerol in a molar ratio of 1:1 to 12:1.

According to another embodiment of the present invention, the acid may be selected from the group consisting of $HNO_3$, HCl, $H_3PO_4$, $CH_3CO_2H$, $H_2CO_3$, HI, $H_2SO_4$, and mixtures thereof.

According to another embodiment of the present invention, step ii) may be performed at a temperature of 140° C. to 200° C. and a pressure of 0.13 kPa to 6.67 kPa.

According to another embodiment of the present invention, in step ii), a Lewis acid metal salt may be further added that is selected from the group consisting of $Zn(NO_3)_2$, $ZnCl_2$, $MgCl_2$, $AlCl_3$, and mixtures thereof.

According to another embodiment of the present invention, in step ii), the reaction may be carried out in a solvent selected from the group consisting of polyethylene glycol dimethyl ether, dibenzyl ether, dibutyl phthalate, and mixtures thereof.

According to another embodiment of the present invention, steps i) and ii) may be performed successively in the same reaction vessel.

According to another embodiment of the present invention, step ii) may be performed in a continuous manner by which the final glycidol is continuously collected under reduced pressure.

According to the method of the present invention, inexpensive and easy-to-purchase acid and base catalysts can be used to produce glycidol from glycerol, a by-product of biodiesel production, as a starting material in high yield with high selectivity in a convenient, simple, and environmentally friendly way. In addition, the method of the present invention eliminates the need to separate the base catalyst.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

The present invention will now be described in more detail.

The present invention is directed to the production of high value-added glycidol from glycerol as a by-product of biodiesel production by combining two steps, i.e. the step of preparing glycerol carbonate from glycerol and the step of producing glycidol from the glycerol carbonate, in a more effective manner. Specifically, the present invention is intended to produce glycidol in high yield with high selectivity by successive reactions in which a base is used as a catalyst in the first step and is allowed to react with an acid to form a salt after the first step, and the salt is used as a catalyst in the second step. Particularly, the base and acid salts are very cheap and easy to purchase. The base catalyst used in the first step can be converted to a salt, which can be used as a catalyst in the second step. Accordingly, there is no need to separate the base catalyst after the first step, resulting in a drastic reduction in cost and time for the overall reactions.

The present invention provides a method for producing glycidol by successive catalytic reactions, including i) reacting glycerol with a dialkyl carbonate to prepare glycerol carbonate, and ii) subjecting the glycerol carbonate to decarboxylation wherein a base is added as a catalyst in step i) and is allowed to react with an acid to form a metal salt after step i), and the salt is used as a catalyst in step ii).

Figure 1:
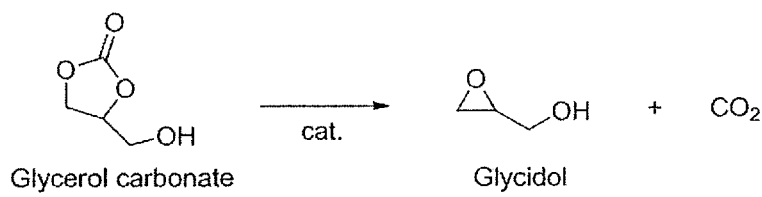
FIG. 1 is a reaction scheme for the production of glycidol by decarboxylation of glycerol carbonate.
Figure 2:
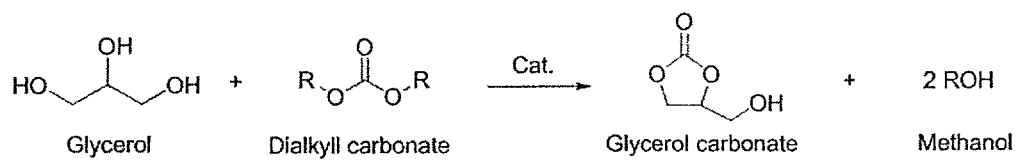
FIGS. 2 and 3 are schematic reaction schemes for the preparation of glycerol carbonate by reacting glycerol with a dialkyl carbonate and urea, respectively.
Figure 3:
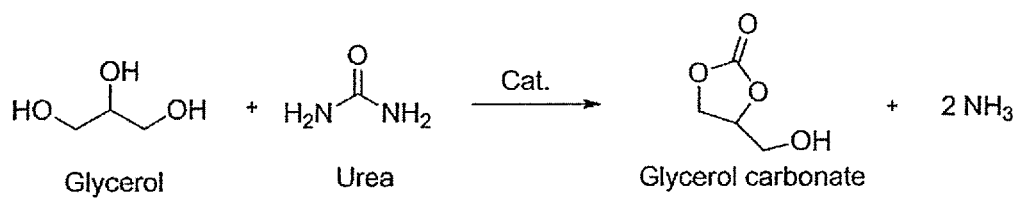

According to the method of the present invention, glycerol reacts with a dialkyl carbonate to prepare glycerol carbonate, as shown in FIG. 2, and the glycerol carbonate is then subjected to decarboxylation. The first step of preparing glycerol carbonate from glycerol is depicted in Reaction Scheme 1:

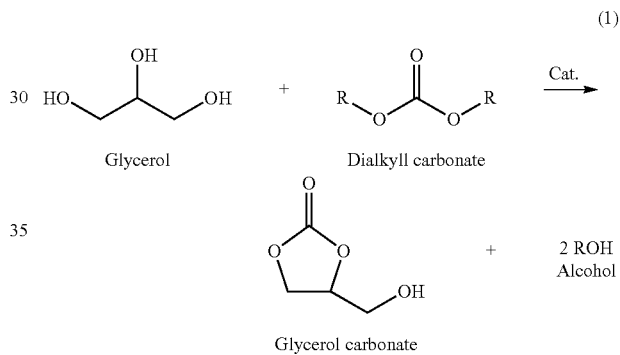

(1)

wherein R is a $C_1$-$C_4$ alkyl group.

Base catalysts were reported to be effective for the reaction of Reaction Scheme 1 (Applied Catalysis A: General 366, (2009), 315-324). The use of relatively cheap and readily commercially available base catalysts is preferred taking into consideration various factors such as production cost saving. Non-limiting examples of such base catalysts include NaOH, KOH, LiOH, and $R_3N$ (R is a $C_2$-$C_6$ alkyl group). These base catalysts may be used alone or as a mixture thereof.

The base catalyst is preferably added in an amount of 0.005 moles to 0.05 moles per mole of the glycerol. If the amount of the base catalyst added is below the lower limit, it takes a long time for the reaction to complete. Meanwhile, the addition of the base catalyst in an amount above the upper limit does not contribute to a further improvement in the yield or rate of the reaction and is thus uneconomical.

A temperature of 20° C. to 90° C. is required for the reaction of Reaction Scheme 1 to proceed. The yield of the glycerol carbonate is lowered at a reaction temperature lower than 20° C. and the amount of by-products increases at a reaction temperature exceeding 90° C.

The reaction is preferably carried out for 3 minutes to 120 minutes. If the reaction time is less than 3 minutes, the yield of the glycerol carbonate is lowered. Meanwhile, even if the reaction time exceeds 120 minutes, the yield of the glycerol carbonate does not increase any more.

In Reaction Scheme 1, 1 mole of the glycerol may react with 1 mole to 12 moles of the dialkyl carbonate. If the amount of the dialkyl carbonate is less than 1 mole, the synthesis yield of the glycerol carbonate may be low. Meanwhile, if the amount of the dialkyl carbonate exceeds 12 moles, the reaction rate may be lowered due to the low concentration of glycerol.

In the second step of the method according to the present invention, the glycerol carbonate is subjected to decarboxylation to yield glycidol. This decarboxylation is depicted in Reaction Scheme 2:

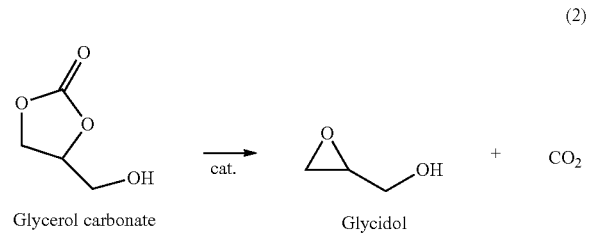 [SMILES: O=C1OCC(CO)O1 ; OCC1CO1 ; "CO2"]

Glycerol carbonate           Glycidol

Various salt catalysts were reported to be effective for the reaction of Reaction Scheme 2 (see Japanese Patent Publication Nos. 2009-137938 and 2009-067689). In the second step of the method according to the present invention, there is no need to separately add the salt catalysts, and instead, an acid is added to the base catalyst remaining after the first step to form a salt catalyst by an acid-base reaction. Accordingly, the method of the present invention eliminates the need for an additional process to remove the base catalyst remaining after the reaction of Reaction Scheme 1 is finished. The residual base catalyst is used as a raw material for the preparation of the catalyst that serves to catalyze the reaction of Reaction Scheme 2. As a result, cost and time for the overall reactions can be drastically reduced, as described previously.

Examples of acids that can be added to form the salt catalyst include, but are not limited to, $HNO_3$, $HCl$, $H_3PO_4$, $CH_3CO_2H$, $H_2CO_3$, $HI$, and $H_2SO_4$. These acids may be used alone or as a mixture thereof.

A temperature of 140° C. to 200° C. and a pressure of 6.67 kPa to 0.13 kPa are required for the reaction of Reaction Scheme 2 to proceed. The yield of glycidol is lowered at a reaction temperature below the lower limit and the selectivity to glycidol is lowered at a reaction temperature above the upper limit. The selectivity to glycidol is lowered at a reaction pressure lower than 0.13 kPa and the reaction is retarded at a reaction pressure exceeding 6.67 kPa.

In the acid addition step, a Lewis acid metal salt may be further added to improve the production yield of glycidol. The reason for the addition of the Lewis acid metal salt is explained by the fact that the Lewis acid metal salt controls the basicity of the reaction solution to effectively suppress side reactions. Specifically, the Lewis acid metal salt is selected from the group consisting of $Zn(NO_3)_2$, $ZnCl_2$, $MgCl_2$, $AlCl_3$, and mixtures thereof.

Figure 4:
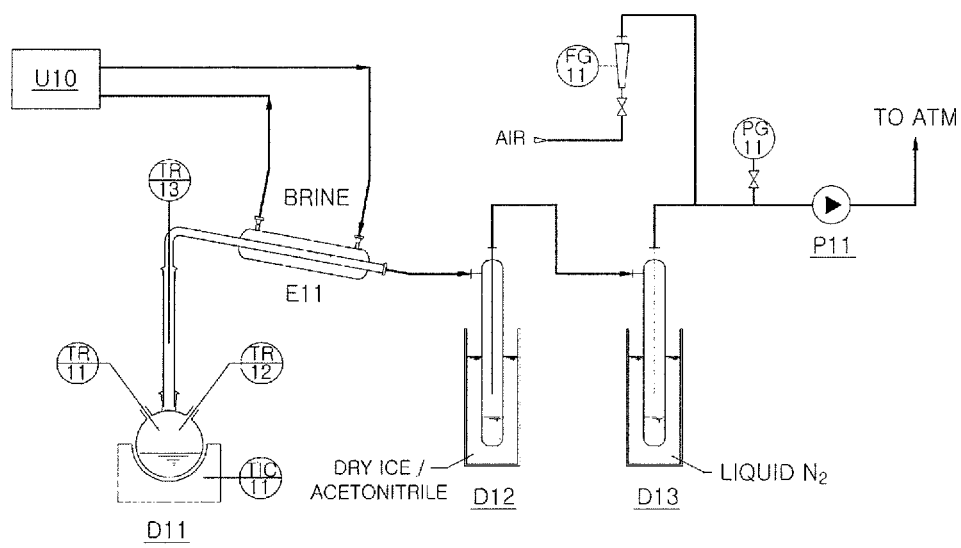
FIG. 4 is a schematic diagram illustrating a system for carrying out a method for glycidol production through a series of reactions according to the present invention.

To further increase the selectivity to glycidol, the reaction of Reaction Scheme 2 is preferably carried out in a solvent that has a high boiling point and can dissolve the glycerol carbonate. The solvent is used to maintain the catalyst concentration at a constant level. Examples of such solvents include, but are not limited to, polyethylene glycol dimethyl ether, dibenzyl ether, and dibutyl phthalate. These solvents may be used alone or as a mixture thereof. It is preferred to perform steps i) and ii) successively in the same reaction vessel in order to maximize the effects of the method according to the present invention. Step ii) is performed in a continuous manner by which the final glycidol is continuously collected under reduced pressure. FIG. 4 illustrates an exemplary system for carrying out the method for glycidol production through the series of reactions according to the present invention.

Referring to FIG. 4, the system includes a reactor D11 equipped with an oil bath for heating reactants, a condenser E11 for condensing vapor generated from the reactor, a product receiver D12 for collecting the condensate and uncondensed components, a cold trap D13 for vapor condensation, and a vacuum pump P11 for reducing the pressure of the reaction system. The system further includes instruments such as a brine circulator U10 for supplying a coolant to the condenser, temperature indicating controllers TR11, TR12, TR13 and TIC for controlling the temperature of the reactor, an air flow meter FG11 for controlling the vacuum level of the reaction system, and a pressure gauge PG11 for measuring the pressure of the reaction system. Glycidol can be produced in the system by the following procedure. First, the acid is added to the synthesized glycerol carbonate. Then, the dialkyl carbonate and methanol are removed. The resulting reaction solution is continuously fed at a rate of 0.2 mL/min into the reaction system through an HPLC pump. In the reaction system, successive reactions for glycidol production can be carried out while continuously collecting the reaction product.

The present invention will be explained in more detail with reference to the following examples. However, these examples are provided to assist in understanding the invention and are not intended to limit the scope of the invention.

Example 1

Preparation of glycerol carbonate 23 g (0.25 mol) of glycerol, 45 g (0.5 mol) of dimethyl carbonate, and 0.203 g of NaOH (corresponding to 2 mol % of glycerol) were placed in a 3-neck flask. The mixture was stirred at 90° C. for 30 min to afford glycerol carbonate.

The temperature of the reactor was controlled using an oil bath. The reaction product was diluted with distilled water. After addition of iso-butanol as an external standard, HPCL quantitative analysis showed that the yield of the glycerol carbonate was 86.30% and the selectivity to the glycerol carbonate was 95.21%.

The yield and selectivity were calculated by the following formulae:

Yield of glycerol carbonate (GLC) (%)=100×Amount of GLC prepared/Amount of glycerol before reaction Selectivity to glycerol carbonate (GLC) (%)=100× Amount of GLC prepared/Amount of glycerol converted after reaction Example 2

Preparation of Glycerol Carbonate Depending on the Kind of Base Catalyst

Glycerol carbonate was synthesized in the same manner as in Example 1, except that kind of the base was changed as shown in Table 1. The results are shown in Table 1.

TABLE 1

| Base | Yield (%) | Selectivity (%) |
|---|---|---|
| NaOH | 86.3 | 95.2 |
| KOH | 83.2 | 94.0 |
| LiOH | 82.9 | 89.7 |
| Et$_3$N | 80.5 | 87.6 |
| Bu$_4$N | 81.9 | 88.6 |

As can be seen from the results in Table 1, the use of NaOH as the base catalyst led to the highest yield (86.3%) of glycerol carbonate. Thus, NaOH was employed as a catalyst for reaction optimization and in a series of reactions for glycidol synthesis.

Example 3

Preparation of Glycerol Carbonate Depending on the Amount of Base Catalyst

Glycerol carbonate was synthesized in the same manner as in Example 1, except that the amount of NaOH (based on glycerol) as a catalyst was changed as shown in Table 2. The yields of glycerol carbonate and the selectivities to glycerol carbonate were analyzed by HPLC and the results are shown in Table 2.

TABLE 2

| Catalyst (mol %) | Yield (%) | Selectivity (%) |
|---|---|---|
| 0.5 | 82.3 | 86.6 |
| 1 | 83.3 | 88.2 |
| 2 | 86.3 | 95.2 |
| 3 | 86.2 | 91.7 |

As can be seen from the results in Table 2, the yield of glycerol carbonate increased from 82.3% to 86.3% with increasing amount of the base catalyst from 0.5 mole % to 2 mole %. However, an additional increase in the amount of the base catalyst to 3 mole % had little influence on the yield of glycerol carbonate.

Example 4

Preparation of Glycerol Carbonate Depending on Reaction Time

Glycerol carbonate was synthesized in the same manner as in Example 1, except that the reaction time was changed as shown in Table 3. The results are shown in Table 3.

TABLE 3

| Reaction time (min) | Yield (%) | Selectivity (%) |
|---|---|---|
| 3 | 63.5 | 92.7 |
| 5 | 76.6 | 93.5 |
| 7 | 84.4 | 90.9 |
| 15 | 86.3 | 92.2 |
| 30 | 86.3 | 95.2 |
| 60 | 86.3 | 92.1 |
| 90 | 86.1 | 92.0 |
| 120 | 86.2 | 91.6 |

As can be seen from the results in Table 3, as the reaction time increased from 3 min to 120 min, the yield of glycerol carbonate increased from 63.5% to 86.2%. The reaction was reached equilibrium within 15 min.

Example 5

Production of Glycidol

The glycerol carbonate prepared in Example 1 was used as a raw material for glycidol synthesis. HNO$_3$ was added in an amount such that the equivalent ratio of the acid to the base catalyst was 1:1. As a result of the reaction, NaNO$_3$ salt was formed. After removal of remaining dimethyl carbonate as the reaction raw material used in Example 1 and methanol as a by-product, the reaction was allowed to proceed in the presence of the salt as a catalyst under a reduced pressure of 2.67 kPa at 175° C. for 3 hr to synthesize glycidol.

After the reaction, an internal standard (HPLC: iso-butanol, GC: DMSO) for the reactant and the product was added. The results of HPLC and GC analyses showed that the yield of glycidol and selectivity to glycidol were 75.2% and 75.6% (based on glycerol), respectively.

The yield and selectivity were calculated by the following formulae:

Yield of glycidol (%)=100×Amount of glycidol produced/Amount of glycerol before reaction Selectivity to glycidol (%)=100×Amount of glycidol produced/Amount of glycerol converted after reaction Example 6

Production of Glycidol Depending on the Kind of Acid

Glycidol was synthesized in the same manner as in Example 5, except that the kind of the acid was changed as shown in Table 4. The results are shown in Table 4.

TABLE 4

| Acid | Yield (%) | Selectivity (%) |
|---|---|---|
| HNO$_3$ | 75.2 | 75.6 |
| HCl | 68.0 | 69.6 |
| H$_2$SO$_4$ | 62.7 | 82.7 |
| H$_3$PO$_4$ | 59.3 | 73.9 |
| CH$_3$CO$_2$OH | 43.0 | 43.5 |
| H$_2$CO$_3$ | 28.5 | 28.6 |
| HI | 74.5 | 74.4 |

As can be seen from the results in Table 4, when the reaction was carried out in the presence of NaNO$_3$ salt, which was formed using HNO$_3$, the yield of glycidol was highest (75.2%).

Example 7

Production of Glycidol with the Addition of Lewis Acid Metal Salt

In this example, Lewis acid metal salts were used to suppress the occurrence of side reactions and improve the yield of glycidol. The reaction was carried out under the same conditions as in Example 5, except that the Lewis acid metal salts listed in Table 5 were added to synthesize glycidol. The results are shown in Table 5.

TABLE 5

| Lewis acid metal salt | Yield (%) | Selectivity (%) |
|---|---|---|
| $Zn(NO_3)_2$ | 78.7 | 85.6 |
| $ZnCl_2$ | 76.9 | 84.9 |
| $SnCl_4$ | 58.9 | 63.6 |
| $AlCl_3$ | 74.5 | 80.4 |
| $MgCl_2$ | 75.6 | 81.9 |

As can be seen from the results in Table 5, the addition of $ZnCl_2$, $Zn(NO_3)_2$ and $MgCl_2$ as the Lewis acid metal salts contributed to an increase in the yield of glycidol while suppressing the occurrence of side reactions. In contrast, $SnCl_4$ decreased the yield of glycidol. This phenomenon indicates that the effect of adding the Lewis acids may vary depending on the kind and/or strength of the metal salts.

Example 8

Production of Glycidol Depending on the Kind of Solvent

Glycidol was synthesized using a solvent having a high boiling point and capable of dissolving glycerol carbonate while maintaining the catalyst concentration at a constant level. The solvent was used to further increase the selectivity to glycidol. After placing the solvent (50 g) and $Zn(NO_3)_2$ in a 250 mL 3-neck flask, $HNO_3$ was added to the glycerol carbonate synthesized in Example 1 and the mixture was continuously fed at a rate of 0.2 mL/min into the reaction system through an HPLC pump. The reaction was allowed to proceed at 2.67 kPa and 175° C. to produce glycidol. The above procedure was repeated except that the solvent was changed to polyethylene glycol dimethyl ether (DMPEG, Mw=350), dibenzyl ether, and dibutyl phthalate. The results are shown in Table 6.

TABLE 6

| Solvent | Yield (%) | Selectivity (%) |
|---|---|---|
| DMPEG[a] | 80.0 | 85.2 |
| DMPEG[b] | 84.7 | 90.4 |
| Dibenzyl ether[a] | 78.7 | 84.0 |
| Dibenzyl ether[b] | 84.5 | 89.6 |
| Dibutyl phthalate[a] | 81.1 | 86.4 |
| Dibutyl phthalate[b] | 83.6 | 89.2 |

[a]Batch reactions using solvent
[b]Successive reactions using solvent

As can be seen from the results in Table 6, the yield of glycidol reached a maximum of about 81% when the batch reactions were carried out using dibutyl phthalate as the solvent. In contrast, the yield of glycidol and the selectivity to glycidol reached maximum values of 84.7% and 90.4%, respectively, when the successive reactions were carried out using DMPEG.

What is claimed is:

1. A method for producing glycidol by successive catalytic reactions, comprising:
   i) reacting glycerol with a dialkyl carbonate to prepare glycerol carbonate; and
   ii) subjecting the glycerol carbonate to decarboxylation,
   wherein a base is added as a catalyst in step i) and is allowed to react with an acid to form a metal salt after step i), and the salt is used as a catalyst in step ii).

2. The method according to claim 1, wherein the base is selected from the group consisting of NaOH, KOH, LiOH, $R_3N$ (R is a $C_2$-$C_6$ alkyl group), and mixtures thereof.

3. The method according to claim 1, wherein in step i), the base catalyst is added in an amount of 0.005 moles to 0.05 moles per mole of the glycerol.

4. The method according to claim 1, wherein step i) is performed at a temperature of 20° C. to 90° C.

5. The method according to claim 1, wherein step i) is performed for 3 minutes to 120 minutes.

6. The method according to claim 1, wherein in step i), the dialkyl carbonate reacts with the glycerol in a molar ratio of 1:1 to 12:1.

7. The method according to claim 1, wherein the acid is selected from the group consisting of $HNO_3$, HCl, $H_3PO_4$, $CH_3CO_2H$, $H_2CO_3$, HI, $H_2SO_4$, and mixtures thereof.

8. The method according to claim 1, wherein step ii) is performed at a temperature of 140° C. to 200° C. and a pressure of 0.13 kPa to 6.67 kPa.

9. A method for producing glycidol by successive catalytic reactions, comprising:
   i) reacting glycerol with a dialkyl carbonate to prepare glycerol carbonate; and
   ii) subjecting the glycerol carbonate to decarboxylation,
   wherein a base is added as a catalyst in step i) and is allowed to react with an acid to form a metal salt after step i), and the salt is used as a catalyst in step ii) and a Lewis acid metal salt is further added that is selected from the group consisting of $Zn(NO_3)_2$, $ZnCl_2$, $MgCl_2$, $AlCl_3$, and mixtures thereof.

10. The method according to claim 1, wherein in step ii), the reaction is carried out in a solvent selected from the group consisting of polyethylene glycol dimethyl ether, dibenzyl ether, dibutyl phthalate, and mixtures thereof.

11. The method according to claim 1, wherein steps i) and ii) are performed successively in the same reaction vessel.

12. The method according to claim 1, wherein step ii) is performed in a continuous manner by which the final glycidol is continuously collected under reduced pressure.

13. The method according to claim 9, wherein the base is selected from the group consisting of NaOH, KOH, LiOH, R3N (R is a C2-C6 alkyl group), and mixtures thereof.

14. The method according to claim 9, wherein in step i), the base catalyst is added in an amount of 0.005 moles to 0.05 moles per mole of the glycerol.

15. The method according to claim 9, wherein in step i), the dialkyl carbonate reacts with the glycerol in a molar ratio of 1:1 to 12:1.

16. The method according to claim 9, wherein the acid is selected from the group consisting of $HNO_3$, HCl, $H_3PO_4$, $CH_3CO_2H$, $H_2CO_3$, HI, $H_2SO_4$, and mixtures thereof.

17. The method according to claim 9, wherein in step ii), the reaction is carried out in a solvent selected from the group consisting of polyethylene glycol dimethyl ether, dibenzyl ether, dibutyl phthalate, and mixtures thereof.

18. The method according to claim 9, wherein steps i) and ii) are performed successively in the same reaction vessel.

19. The method according to claim 9, wherein step i) is performed in a continuous manner by which the final glycidol is continuously collected under reduced pressure.

20. A method for producing glycidol by successive catalytic reactions, comprising:
   i) reacting glycerol with a dialkyl carbonate to prepare glycerol carbonate; and
   ii) subjecting the glycerol carbonate to decarboxylation,
   wherein a base selected from the group consisting of NaOH, KOH, LiOH, $R_3N$ (R is a $C_2$-$C_6$ alkyl group), and mixtures thereof is added as a catalyst in step i) and is allowed to react with an acid selected from the group consisting of $HNO_3$, HCl, $H_3PO_4$, $CH_3CO_2H$, $H_2CO_3$, HI, H₂SO₄, and mixtures thereof to form a metal salt after step i), and the salt is used as a catalyst in step ii) and a Lewis acid metal salt is further added that is selected from the group consisting of $Zn(NO_3)_2$, $ZnCl_2$, $MgCl_2$, $AlCl_3$, and mixtures thereof.

\* \* \* \* \*